US006885810B2

(12) United States Patent
Allwohn et al.

(10) Patent No.: US 6,885,810 B2
(45) Date of Patent: Apr. 26, 2005

(54) ELECTRICALLY HEATED HAIR DRYER WITH CATALYTIC ODOR FILTER

(75) Inventors: Juergen Allwohn, Burgschwalbach (DE); Detlef Mattinger, Bickenbach (DE); Stefan Uhl, Darmstadt (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/467,156

(22) PCT Filed: Feb. 6, 2002

(86) PCT No.: PCT/EP02/01210

§ 371 (c)(1),
(2), (4) Date: Nov. 17, 2003

(87) PCT Pub. No.: WO02/063991

PCT Pub. Date: Aug. 22, 2002

(65) Prior Publication Data

US 2004/0071455 A1 Apr. 15, 2004

(30) Foreign Application Priority Data

Feb. 10, 2001 (DE) .......................... 101 06 109

(51) Int. Cl.$^7$ .............................. F24H 3/00; A45D 20/00
(52) U.S. Cl. ...................... 392/385; 392/410; 392/380; 34/97; 34/99; 422/22; 422/177
(58) Field of Search ................. 392/379–385, 392/360–365, 410; 55/DIG. 30; 422/174, 177, 22; 219/553; 34/96–101

(56) References Cited

U.S. PATENT DOCUMENTS

| | | | | |
|---|---|---|---|---|
| 2,873,071 A | * | 2/1959 | Bratton ........................ 237/2 R |
| 3,289,679 A | * | 12/1966 | Zellerman .................... 132/208 |
| 4,023,928 A | * | 5/1977 | Haensel ........................ 422/49 |
| 4,323,761 A | * | 4/1982 | Hubner ........................ 392/410 |
| 4,626,659 A | * | 12/1986 | Charmes et al. ............. 392/408 |
| 5,195,165 A | * | 3/1993 | Ono et al. ................... 392/407 |
| 6,034,354 A | * | 3/2000 | Hironaka ..................... 219/383 |
| 6,130,991 A | * | 10/2000 | Chapman ..................... 392/367 |

FOREIGN PATENT DOCUMENTS

| | | |
|---|---|---|
| DE | 2 010 075 | 9/1971 |
| DE | 23 63 820 A | 6/1975 |
| DE | 3223440 | * 12/1983 |
| DE | 199 15 377 A1 | 10/2000 |
| DE | 199 15 377 A | 10/2000 |
| EP | 0 176 003 A | 4/1986 |
| EP | 0 176 003 B1 | 6/1991 |
| EP | 0 695 552 B1 | 9/1999 |
| EP | 0 695 521 B1 | 10/1999 |
| JP | 62-119362 | * 5/1987 |
| JP | 63-118557 | * 5/1988 |
| JP | 3-241264 | * 10/1991 |
| JP | 9-201403 | * 8/1997 |
| JP | 10-162942 | * 6/1998 |
| JP | 10-246512 | * 9/1998 |

* cited by examiner

Primary Examiner—John A. Jeffery
(74) Attorney, Agent, or Firm—Michael J. Striker

(57) ABSTRACT

The handheld hair dryer for generating a heated air stream has a blower for generating an air stream, an electric heater for heating the air stream, a catalytic odor filter for deodorizing the air stream and a thermal radiator for heating the catalytic odor filter. The electric heater and the catalytic odor filter are separate from each other so that the active surface area of the catalytic odor filter can be maximized to deodorize the air stream. The thermal radiator is also separate from the electric heater.

2 Claims, 1 Drawing Sheet

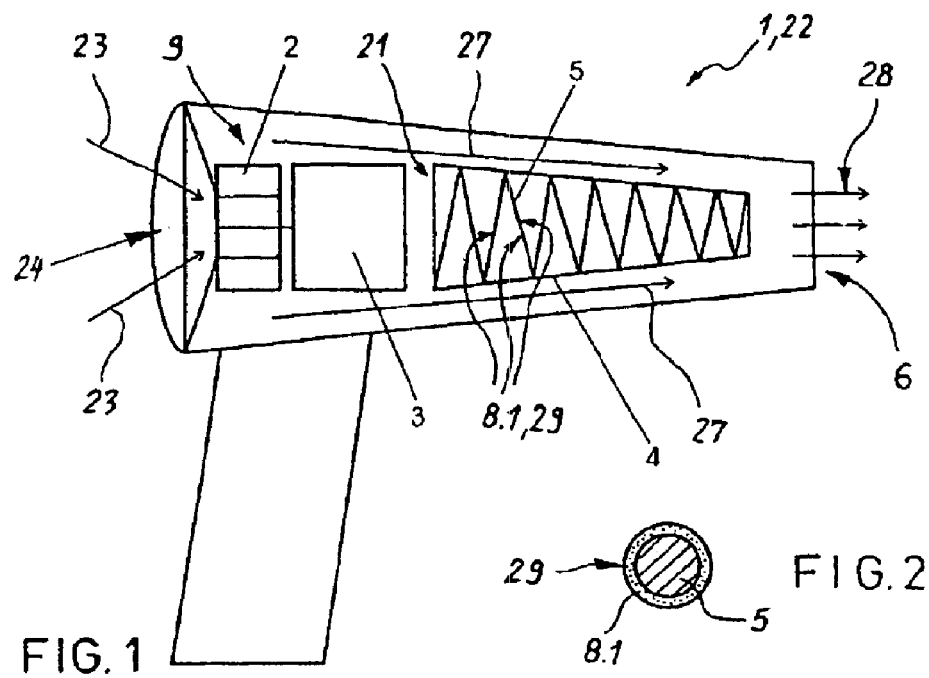
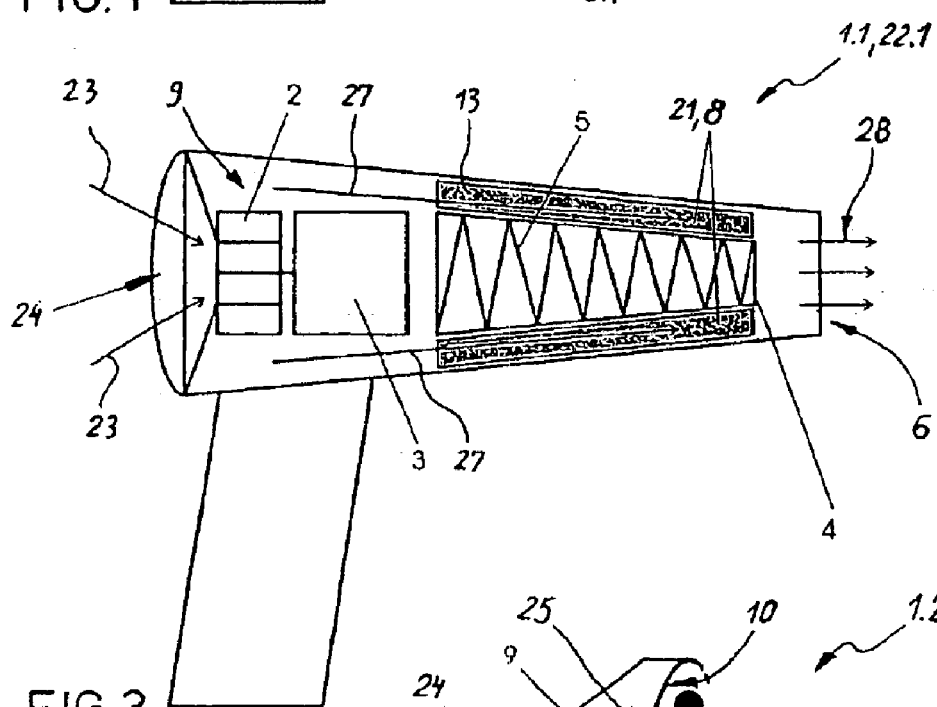
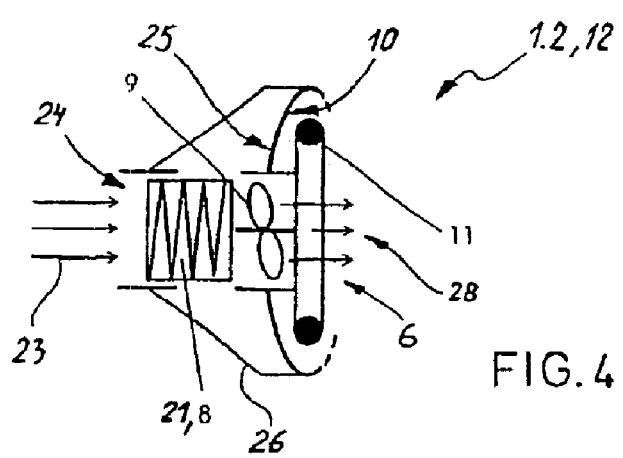
FIG. 1
FIG. 2
FIG. 3
FIG. 4

ELECTRICALLY HEATED HAIR DRYER WITH CATALYTIC ODOR FILTER

The invention relates to a hair dryer of the generic type having an electric heater and a blower for generating a stream of heated air.

Hot-air devices with a heater and blower for drying or heat treatment of hair on the head or for drying wet hands after they have been washed or for heating a room (fan heaters) are known in a very wide range of designs, for example as a hair-dryer (handheld hair-dryer/drying and styling of hair) or, from EP 0 176 003 B1, as a hood-type hair-dryer (permanent waving or coloring/bleaching of hair) or, from EP 0 695 521 B1, as a device of open structure (permanent waving or coloring/bleaching of hair), as known as the model "Climazon Millenium" produced by the applicant through prior public use. Devices of this type generally operate reliably and fulfill their intended purpose.

The invention is based on the object of providing a hair dryer of the generic type having an electric heater and a blower for generating a stream of heated air, which also deodorizes the air stream and which has a simple, structure.

In a hairdressing salon, there is often an unpleasant mix of a very wide range of odor substances, typically ammonia and perfumes. In addition to the nuisance to customers and hairdressers caused by the odor, the above substances constitute a certain risk of allergies in particular for the hairdressing staff. Effective cleaning of the room air in the salon increases customer comfort and noticeably improves working conditions. Various room-air cleaners are offered to the hairdresser for this purpose. A drawback of this equipment is that it costs additional money, consumes energy, takes up space and also requires a dedicated power supply.

The abovementioned drawbacks are resolved by integrating a catalytic filter in a hot-air device of the generic type, for example for treating the hair on the head or drying hands or heating a room. Particularly in the case of handheld hair-dryers, hood-type hair-dryers, "Climazon Millenium" and fan heaters, the multiple use results in synergies which make these additional benefits particularly economic and efficient. The need for a separate air cleaner is also eliminated as a result. This also results in new generations of equipment with a new, additional functionality; by way of example, the hairdresser automatically cleans the air in the salon during his everyday work using the device, or alternatively so do users of a hand-dryer, which is usually arranged in a fixed position on a room wall, for example of a public-toilet. In an electric fan heater too, the room air is cleaned at the same time.

The subject of the invention is a hot-air device with integrated, catalytic odor filter, in which optionally the device components blower/heater or alternatively only the blower are additionally utilized or provided with an air-cleaning functionality. Catalysts which are intended to break down odor substances in the air require a high operating temperature and, with a view to efficiency, a high air throughput. Both conditions are already ideally present in a hair-dryer, a hood-type hair-dryer, a "Climazon Millenium", a hand-dryer or a fan heater. The operating temperature of the catalyst is ensured by thermal coupling to the heater element. The heater wire is preferably directly coated with the catalytically active substance. However, it is also conceivable for a separate catalyst filter element to be arranged sufficiently close to the heater to ensure that the operating temperature is reached. It is also possible for this element to be equipped with a dedicated heating means if this has design benefits. In this case, the waste heat which is generated is additionally used to heat the air stream. The required air throughput is automatically ensured, since the filter element is integrated directly in the air flow path of the device. The combination of a filter of this type with a hot-air device used by hairdressers (handheld hair-dryer, hood-type hair-dryer, "Climazon Millenium", hand-dryer (offers the hairdresser an inexpensive and practical way of improving the air in his salon.

In the case of a hood-type hair-dryer having an air circulation device, in which approximately 60% of the air is returned to the hood-type hair-dryer (DE 201 007 5 A and EP 0 176 003 B1), a catalytic odor filter also has the particular advantage that a person sitting beneath the hood-type hair-dryer is continuously exposed to odor-filtered room air.

The invention is described in more detail with reference to three different, diagrammatically depicted exemplary embodiments. In the drawing:

FIG. 1 shows a first exemplary embodiment of a handheld hair-dryer with a catalytic odor filter;

FIG. 2 shows a sectional illustration of an individual heater wire, illustrated on an enlarged scale, with a coating of catalyst substance;

FIG. 3 shows a second exemplary embodiment of a handheld hair-dryer with a catalytic odor filter; and FIG. 4 shows a third exemplary embodiment of a hood-type hair dryer with a thermal radiator with blower and a catalytic filter.

FIG. 1 shows a hot-air device 1 with an integrated catalytic odor filter 21 on the basis of a typical handheld hair-dryer 22, which is diagrammatically illustrated, as a first exemplary embodiment. The functional and design principles and the basic idea of the invention can be transferred to other hot-air devices, such as for example hood-type hair-dryers and radiation appliances with air stream drying (EP 0 695 521 B1), hand-dryers and fan heaters. Differences consist in the dimensions of individual elements and in design details, such as for example the air guidance (return air in hood-type hair-dryers) and the design of a heater 4. The functional elements and their basic arrangement remain the same. In the case of a hot-air device 1 which is designed as a handheld hair-dryer 22, outside air 23 is sucked in via an air inlet 24 by an impeller 2 which is driven by a motor 3, a blower air stream 27 being guided over the heater 4 and blown out through the air outlet 6 as a hot-air stream 28. A handheld hair-dryer 22 of this type already has all the basic features required for a catalytic odor filter 21: there is a high throughput of air and a significantly increased temperature at at least one location in the region where air is carried. The air throughput is required in order to allow the room air to be cleaned as thoroughly as possible and to ensure the high temperature which is required in order for a catalyst (catalytic air filter 21) to function. To make the desired catalytic reactions efficient, the catalytically active surface 21, should have optimum thermal coupling to the heater 4. This is preferably achieved by the heater 4 itself or only, parts thereof, such as for example the heater wire 5, being directly provided with a coating of catalytic substance 8.1 or at least partially consisting of such a substance (FIG. 2), the odor filter 21 with the coating of catalytic substance 8.1 being acted on by the blower air stream 27. A coating of catalytic substance 8.1 of this type is known, for example, from DE 199 153 77 A1 (which is therefore considered to be completely disclosed) as a catalytic composition for deodorizing or oxidation purposes, comprising a coating made from a coating compound on a support and obtainable by application of the coating compound, including a polycondensate comprising (A) one or more silanes of the general formula

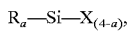

where the radicals R are identical or different and represent non-hydrolizable groups, the radicals X are identical or different and are hydrolizable groups or hydroxyl groups, and a is 0, 1, 2 or 3, a being greater than 0 if the silanes form at least 50% by substance quantity, or an oligomer derived therefrom, (B) if appropriate one or more compounds of glass-forming elements, and particles of one or more transition metal oxides, the weight ratio of transition metal oxide particles to polycondensate being 10:1 to 1:10, to the support and heat-treatment of the coating compound which has been applied.

Moreover, it is possible and appropriate to provide all the air-carrying regions of a hot-air device 1, 1.1, 1.2 with catalytically active surfaces, provided that in operation they reach a temperature which is sufficient for activation of the catalyst 8.

In a secondary exemplary embodiment, shown in FIG. 3, a separate catalyst 8 of independent structure is integrated in the airway of a handheld hair-dryer 22.1, so that this structure has a large surface area and the blower air stream 27 passes thoroughly around it. On the one hand, this may be appropriate for maximizing an active surface area. On the other hand, it may be appropriate in the case of heaters 4 which are not primarily used for air heating, but rather, for example as shown in FIG. 4, are designed as thermal radiators 12 with a quartz radiator 11, in a similar manner to those described, for example, in EP 0 695 521 B1. In this case, the separate catalyst element 8 may either be thermally passively coupled to a heater 4 or may itself be actively heated by means of a separate thermal radiator 13 and acted on by the air stream from the blower.

In a third exemplary embodiment, shown in FIG. 4, a blower 9 sucks in outside air 23 over a separate catalyst element 8. The quartz radiator 11, which is in this case of annular design, in a housing 26 is not primarily designed for air heating. This takes place primarily as a result of the heat lost at the rear side 25 of a reflector 10. If the catalyst 8 or odor filter 21 is additionally heated, in order to reach the required operating temperature, this contributes to the heating of the air which is in any case desired. The odor filter 21 shown in FIGS. 3 and 4 is designed in such a manner that it can be removed for cleaning purposes.

Further catalyst materials or catalyst coatings 8.1 or preferred embodiments of catalyst elements 8 are not described in more detail in the present text, since they are sufficiently known from the prior art, for example from DE 199 153 77 A1. However, materials which on the one hand break down the odor substances which are encountered in a hairdressing salon, such as for example ammonia, mercaptans and perfumes, as successfully as possible and at the lowest possible temperatures and, on the other hand, can easily and inexpensively be applied to typical heating elements and/or other surfaces in the air-carrying path of a hot-air device 1, are particularly suitable. They should have good and permanent adhesion and should not impair the performance and service life of the heaters 4.

What is claimed is:

1. A handheld hair dryer for generating a heated stream of air, said handheld hair dryer comprising a blower for generating an air stream;

an electric heater for heating said air stream;

a catalytic odor filter for deodorizing said air stream; and a thermal radiator for heating said catalytic odor filter;

wherein said electric heater and said catalytic odor filter are separate from each other and arranged to act on said air stream in order to heat and deodorize said air stream and wherein said thermal radiator is separate from said electric heater.

2. The handheld hair dryer as defined in claim 1, wherein said catalytic odor filter is removable from the hair dryer for cleaning.

* * * * *